United States Patent
Thompson

(10) Patent No.: US 9,339,398 B2
(45) Date of Patent: May 17, 2016

(54) RADIOPAQUE ENHANCED NICKEL ALLOY FOR STENTS

(71) Applicant: Medtronic Vascular, Inc., Santa Rosa, CA (US)

(72) Inventor: Dustin Thompson, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 759 days.

(21) Appl. No.: 13/772,211

(22) Filed: Feb. 20, 2013

(65) Prior Publication Data

US 2013/0289705 A1    Oct. 31, 2013

Related U.S. Application Data

(60) Provisional application No. 61/639,031, filed on Apr. 26, 2012.

(51) Int. Cl.
| | |
|---|---|
| *C22C 19/05* | (2006.01) |
| *A61F 2/82* | (2013.01) |
| *A61L 31/02* | (2006.01) |
| *A61L 31/18* | (2006.01) |
| *C22C 30/00* | (2006.01) |
| *C22F 1/10* | (2006.01) |
| *B23K 35/30* | (2006.01) |
| *B23K 35/02* | (2006.01) |
| *C22C 1/02* | (2006.01) |

(52) U.S. Cl.
CPC .................. *A61F 2/82* (2013.01); *A61L 31/022* (2013.01); *A61L 31/18* (2013.01); *B23K 35/0266* (2013.01); *B23K 35/3033* (2013.01); *C22C 1/02* (2013.01); *C22C 19/051* (2013.01); *C22C 19/055* (2013.01); *C22C 19/056* (2013.01); *C22C 30/00* (2013.01); *C22F 1/10* (2013.01)

(58) Field of Classification Search
CPC ........ C22C 19/055; C22C 19/056; C22F 1/10
See application file for complete search history.

(56) References Cited

U.S. PATENT DOCUMENTS

| | | | |
|---|---|---|---|
| 5,858,556 | A | 1/1999 | Eckert et al. |
| 5,983,951 | A | 11/1999 | Tanguchi et al. |
| 6,027,528 | A | 2/2000 | Tomonto et al. |

(Continued)

FOREIGN PATENT DOCUMENTS

| | | |
|---|---|---|
| EP | 1657318 | 5/2006 |
| JP | 2000104141 | 4/2000 |

(Continued)

OTHER PUBLICATIONS

English Abstract of Nakayama et al. (JP 2003-166026) (Jun. 13, 2003).*

*Primary Examiner* — Jessee Roe

(57) ABSTRACT

A stent includes a nickel-based alloy that includes 10-35 weight % metal member selected from the group consisting of platinum (Pt), gold (Au), iridium (Ir), osmium (Os), rhenium (Re), palladium (Pd), tantalum (Ta), and combinations thereof; 0-6 weight % cobalt (Co); 17-24 weight % chromium (Cr); 13-15 weight % tungsten (W); 0-3 weight % molybdenum (Mo); 0-5 weight % iron (Fe); and balance nickel (Ni). The nickel-based alloy may be a thin outer shell of a hollow stent. The nickel-based alloy may be used to form at least one of an inner core and an outer shell of a core-shell structure of a stent.

17 Claims, 7 Drawing Sheets

(56) References Cited

U.S. PATENT DOCUMENTS

| | | |
|---|---|---|
| 6,248,190 B1 | 6/2001 | Stinson |
| 6,419,693 B1 | 7/2002 | Fariabi |
| 6,497,709 B1 | 12/2002 | Heath |
| 6,527,802 B1 | 3/2003 | Mayer |
| 6,746,478 B2 | 6/2004 | Jayaraman |
| 7,250,058 B1 | 7/2007 | Pacetti et al. |
| 7,329,383 B2 | 2/2008 | Stinson |
| 7,445,749 B2 | 11/2008 | Craig |
| 7,540,997 B2 | 6/2009 | Stinson |
| 7,780,798 B2 | 8/2010 | Stinson et al. |
| 2003/0018380 A1 | 1/2003 | Craig et al. |
| 2003/0194343 A1 | 10/2003 | Craig |
| 2004/0129347 A1 | 7/2004 | Craig |
| 2005/0145508 A1 | 7/2005 | Larsen et al. |
| 2006/0147334 A1 | 7/2006 | Cascone |
| 2007/0135734 A1 | 6/2007 | Reynolds et al. |
| 2007/0189917 A1 | 8/2007 | Stinson |
| 2010/0004726 A1 | 1/2010 | Hancock et al. |
| 2010/0145268 A1 | 6/2010 | Stinson |

FOREIGN PATENT DOCUMENTS

| | | |
|---|---|---|
| JP | 2003166026 | 6/2003 |
| WO | WO01/72349 | 10/2001 |
| WO | WO2005039663 | 5/2005 |
| WO | WO2008024537 | 2/2008 |

* cited by examiner

RADIOPAQUE ENHANCED NICKEL ALLOY FOR STENTS

CROSS-REFERENCE TO RELATED APPLICATIONS

This application claims the benefit of priority from U.S. Provisional Patent Application Ser. No. 61/639,031, which was filed on Apr. 26, 2012 and is incorporated herein by reference in its entirety.

FIELD

The present invention is related to nickel-based alloys that are used to manufacture implantable medical devices, such as stents.

BACKGROUND

A stent is typically a hollow, generally cylindrical device that is deployed in a body lumen from a radially contracted configuration into a radially expanded configuration, which allows it to contact and support a vessel wall. A plastically deformable stent may be implanted during an angioplasty procedure by using a balloon catheter bearing a compressed or "crimped" stent, which has been loaded onto the balloon. The stent radially expands as the balloon is inflated, forcing the stent into contact with the body lumen, thereby forming a support for the vessel wall. Deployment is effected after the stent has been introduced percutaneously, transported trans-luminally, and positioned at a desired location by means of the balloon catheter.

Stents may be formed from wire(s) or strip(s) of material, may be cut from a tube, or may be cut from a sheet of material and then rolled into a tube-like structure. As new generations of stents become thinner in strut dimension/thickness, many metal alloys that have historically been used for stents may not have enough radio-density, or radiopacity, for appropriate visualization under fluoroscopy or x-ray, which may be used to visualize the location of the stent as it is transported trans-luminally.

SUMMARY

It is desirable to develop materials for implantable medical devices, such as stents, to provide enhanced radiopacity, while retaining or improving mechanical properties including, but not limited to, mechanical strength, toughness, durability, flexibility, deliverability, minimal recoil, ductility, and/or corrosion resistance, of materials that are currently used for such implantable medical devices.

According to an aspect of embodiments of the present invention, there is provided a stent that includes a nickel-based alloy comprising 10-35 weight % metal member selected from the group consisting of platinum (Pt), gold (Au), iridium (Ir), osmium (Os), rhenium (Re), palladium (Pd), tantalum (Ta), and combinations thereof; 0-6 weight % cobalt (Co); 17-24 weight % chromium (Cr); 13-15 weight % tungsten (W); 0-3 weight % molybdenum (Mo); 0-5 weight % iron (Fe); and balance nickel (Ni).

According to an aspect of embodiments of the present invention, there is provided a stent that includes a plurality of struts formed by a wire. The wire includes an outer shell surrounding an inner core. At least one of the outer shell and the inner core includes a nickel-based alloy. The nickel-based alloy includes 10-35 weight % metal member selected from the group consisting of platinum (Pt), gold (Au), iridium (Ir), osmium (Os), rhenium (Re), palladium (Pd), tantalum (Ta), and combinations thereof; 0-6 weight % cobalt (Co); 17-24 weight % chromium (Cr); 13-15 weight % tungsten (W); 0-3 weight % molybdenum (Mo); 0-5 weight % iron (Fe); and balance nickel (Ni).

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION

Figure 1:
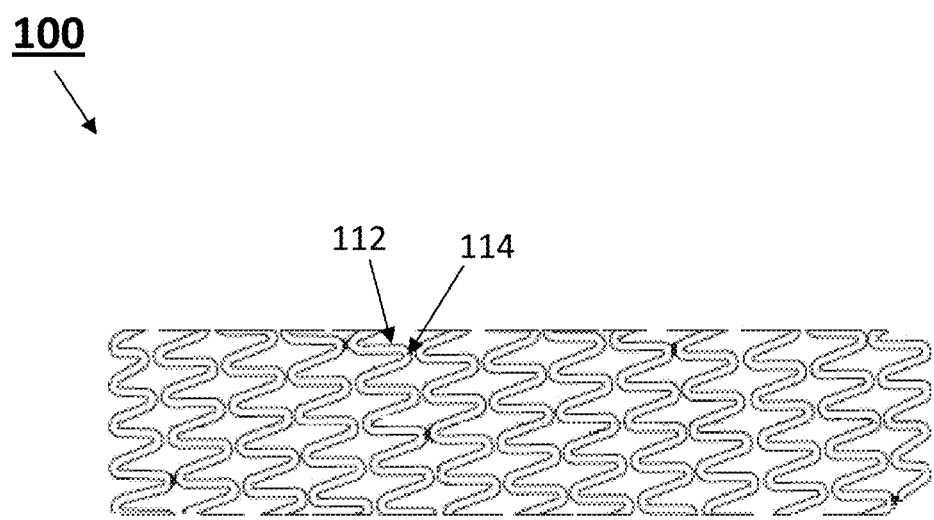
FIG. 1 depicts a stent having struts and crowns in accordance with various embodiments of the present invention.

Embodiments of the present invention are directed to an inventive Ni-based alloy to achieve enhanced radiopacity, while retaining or improving other properties, such as mechanical properties.

According to embodiments of the invention, the Ni-based alloys may include one metal element that has a density and/or atomic number that is greater than the other metal elements in commercially available Ni-based alloys. Examples of existing Ni-based alloys may include those having trade name of Haynes, and/or other Ni-containing alloys known in the art. For example, Haynes 230 is generally known to have a typical composition of about 57% nickel (Ni), about 5% cobalt (Co), about 22% chromium (Cr), about 2% molybdenum (Mo), about 14% tungsten (W), and about 3% iron (Fe) by weight.

As noted above, according to embodiments of the invention, at least one metal element that has a density or atomic number that is greater than the other metal elements in commercially available Ni-based alloys, such as the Haynes 230 alloy listed above, may have a density of about 12 g/cm$^3$ or higher. For convenience, the term "dense metal member" or "elemental dense metal" will be used to describe such an element, and may include, without limitation, platinum (Pt), gold (Au), iridium (Ir), osmium (Os), rhenium (Re), tungsten (W), palladium (Pd) and/or tantalum (Ta). In some embodiments, the dense metal member may be Pt or a Pt-containing alloy, such as PtIr. In other embodiments, the dense metal member may be formed by elemental dense metal(s) other than Pt.

As compared with existing or conventional Ni-based alloys, the Ni-based alloys according to embodiments of the invention may have a composition that has a reduced content of nickel (Ni) and/or other metals, while the content of remaining metal(s) in the existing Ni-based alloys may or may not be reduced. In an embodiment, Ni and/or other metals in the existing Ni-based alloys may be at least partially replaced by the disclosed dense metal member, and/or their alloys. In an embodiment, the disclosed Ni-based alloys may be formed including dense metal member(s) with the existing Ni-based alloys, wherein the material ratio between metals in the existing Ni-based alloys is maintained.

In a specific example, Pt and its alloys may be used as the dense metal member to partially replace the content of Ni or may be balanced by known composition of the existing Ni-based alloy, to form the Ni-based alloy in accordance with embodiments of the invention for providing desired properties. Both Pt and Ni are transition metals with a face cubic centered (FCC) structure known to provide ductility without affecting properties or characteristics of the final alloy and to be an austenite stabilizer. In another example, Pt may be added into, e.g., melted into Haynes 230.

In an exemplary embodiment, the nickel-based alloy used to form a stent may include, but not be limited to,
  10-35 weight %, for example, 10-25, 10-20, or about 20 weight % dense metal member;
  0-6 weight % cobalt (Co);
  17-24 weight % chromium (Cr);
  13-15 weight % tungsten (W);
  0-3 weight % molybdenum (Mo);
  0-5 weight % iron (Fe); and
  balance nickel (Ni).
In an embodiment, the dense metal member comprises platinum (Pt).

In an exemplary embodiment, the nickel-based alloy used to form a stent may include, for example,
  10-25 weight % dense metal member;
  4-6 weight % cobalt (Co);
  17-23 weight % chromium (Cr);
  13-15 weight % tungsten (W);
  2-3 weight % molybdenum (Mo);
  0-3 weight % iron (Fe); and
  balance nickel (Ni).
In an embodiment, the dense metal member comprises platinum (Pt).

In an exemplary embodiment, the nickel-based alloy used to form a stent may include, for example,
  about 20 weight % dense metal member;
  about 5 weight % cobalt (Co);
  about 22 weight % chromium (Cr);
  about 14 weight % tungsten (W);
  about 2 weight % molybdenum (Mo);
  about 3 weight % iron (Fe); and
  balance nickel (Ni).
In an embodiment, the dense metal member comprises platinum (Pt).

In an exemplary embodiment, the nickel-based alloy used to form a stent may include, for example,
  about 21 weight % dense metal member;
  about 5 weight % cobalt (Co);
  about 18 weight % chromium (Cr);
  about 13 weight % tungsten (W);
  about 2 weight % molybdenum (Mo);
  about 4 weight % iron (Fe); and
  balance nickel.
In an embodiment, the dense metal member comprises platinum (Pt).

The Ni-based alloys disclosed herein may be used to form the wires, sheets, and tubes from which stents with desired properties, as described herein, are formed.

FIG. 1 depicts a stent 100 according to an embodiment of the invention that includes a plurality of struts 112 and a plurality of crowns or turns 114, with each crown or turn 114 connecting a pair of adjacent struts 112. The stent 100 may be formed from a tube or wire using methods known in the art, and the tube or wire used to form the stent 100 may be made from materials in accordance with embodiments of the invention. For example, if a tube is used to form a stent, the tube may be cut with a laser or etched with the pattern of the stent by known methods. If a wire is used to form a stent, the wire may be formed into a generally sinusoidal waveform, and wrapped around a mandrel or rod. Select neighboring crowns may be fused together, and the ends of the wire may be cut by a laser where the stent terminates.

Figure 2A:
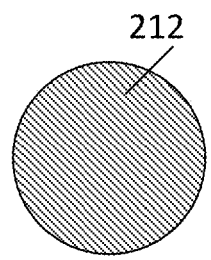
FIGS. 2A and 2B depict cross-sections of various exemplary struts of stents in accordance with various embodiments of the present invention.
Figure 2B:
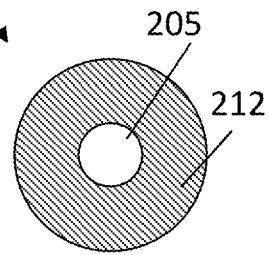

FIGS. 2A and 2B depict cross-sections of struts of stents 200A, 200B, respectively, in accordance with embodiments of the invention.

In FIG. 2A, a Ni-based alloy 212 according to embodiments of the invention as disclosed herein may be used to form a wire used to form the struts of the stent 200A having the desired radiopacity, mechanical properties, and/or other properties.

In FIG. 2B, the stent 200B may be formed from a wire that includes an outer shell formed of the disclosed Ni-based alloy 212. The outer shell may substantially surround an inner core, which is a hollow inner core 205 in this embodiment, forming an open lumen. In embodiments, the outer shell may be thin having a thickness of about 0.0010 inches or less or ranging from about 0.0005 to about 0.0020 inches due to use of the disclosed Ni-based alloy 212 to sufficiently provide desired radiopacity and/or mechanical properties.

Figure 2C:
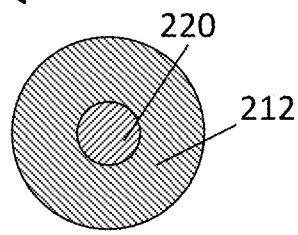
FIGS. 2C and 2D depict cross-sections of various exemplary composite struts of stents in accordance with various embodiments of the present invention.
Figure 2D:
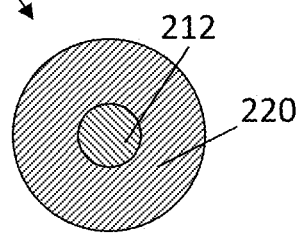

FIGS. 2C and 2D depict cross-sections of composite struts of stents 200C, 200D, respectively, in accordance with embodiments of the invention. Composite struts/stents may utilize different performance characteristics of individual materials to improve their overall performance.

In FIG. 2C, the exemplary struts of stent 200C may be formed to include an outer shell formed of the Ni-based alloy 212 substantially surrounding an inner core formed by a metal member 220. The metal member 220 may be selected to provide desired properties. The metal member may include at least one metal and may be a metal alloy. The metal member 220 surrounded by the Ni-based alloy 212 may or may not be a dense metal member. However, when a dense metal member is used for the metal member 220, the struts of stent 200C in FIG. 2C may have even further enhanced radiopacity while retaining (or improving) other properties, as disclosed herein.

In FIG. 2D, the metal member 220, such as a dense metal member, may be used as an outer shell substantially surrounding an inner core of the disclosed Ni-based alloy 212 to form struts of stent 200D that has the desired radiopacity and other properties, depending the materials selected and used.

In embodiments, the dense metal member 220 may be about 20% to about 45% by weight of the total wire including the dense metal member 220 and the Ni-based alloy 212 as depicted in FIGS. 2C and 2D. For example, in an embodiment, the dense metal member 220 of FIG. 2C may be PtIr, and the diameter of the core of PtIr may be about 10-25% of the diameter of the wire. In an embodiment, the dense metal member 220 of FIG. 2C may be tantalum (Ta), and the diameter of the core of the Ta 220 may be about 10-30% of the diameter of the wire.

Although the cross-sections depicted in FIGS. 2A-2D are circular for illustration purposes, one of ordinary skill in the art would appreciate that other possible cross-sections, regular or irregular, including a triangle, a square, a rectangle, a polygon, oval, etc., may be used for the disclosed alloys/wires/tubes/struts/stents. In addition, the core-shell structures shown in FIGS. 2B-2D may be formed coaxially or non-coaxially, while the outer shell and the inner core may have the same or different cross-sectional shapes.

The following examples are illustrative of embodiments of the invention and not intended to be limiting.

EXAMPLES

Ni-based alloys with certain exemplary compositions as disclosed herein were draw down to about 0.0033" (0.084 mm) on spools and melted for analysis. Melt analysis was conducted with energy dispersive (ED)-XRF spectrometers, which include, for example, x-Ray generator, x-Ray tube, HV supply, vacuum system, pulse processor, Si (Li) detector, targets, PC, MCA, printer, etc., to provide a concentration measurement of each element in the Ni-based alloy samples. As measured, the higher the intensity of the signal, the higher the concentration of an element in the Ni-based alloy samples. Preliminary evaluations revealed desired mechanical strength and ductility when compared to conventionally utilized stainless steel alloys, Ni-based alloys, or other alloys.

Example 1

Table I lists alloy compositions (by weight) for a Ni-based alloy in Example 1:

TABLE I

Ni-Based Alloy

| Element | Wt. % |
| --- | --- |
| Cr | 22 |
| Co | 5 |
| Fe | ≤3 |
| Mo | 2 |
| Ni | Remainder |
| Pt | 15-25 |
| W | 14 |

Example 2

Table II lists alloy compositions (by weight) for a Ni-based alloy in Example 2:

TABLE II

Ni-Based Alloy

| Element | Wt. % |
| --- | --- |
| Cr | 22 |
| Co | 5 |
| Fe | 3 |
| Mo | 2 |
| Ni | Remainder |
| Pt | 20 |
| W | 14 |

Example 3

Table III lists exemplary alloy compositions (in weight %) for each of exemplary Ni-based alloys H1a, H1b, H2a, and H2b, and a commercially available Ni-based alloy, Haynes 230:

TABLE III

Ni-based Alloys

| Element Samples | Element wt-% | | Element wt-% (with Ta-core) | | Element wt-% Haynes 230 |
| --- | --- | --- | --- | --- | --- |
| | H1a | H1b | H2a | H2b | |
| Co | 5 | 4.9 | 5 | 5.4 | 5 |
| Cr | 22 | 17.7 | 22 | 22.9 | 22 |
| W | 14 | 13.3 | 14 | 14.8 | 14 |
| Mo | 2 | 2.2 | 2 | 2.4 | 2 |
| Fe | 3 | 4.4 | 3 | 3.8 | 3 |
| Ni | 34 | 37.1 | 34 | 39.8 | 57 |
| Pt | 20 | 21 | 20 | 11.3 | n/a |

Specifically, Table III compares Ni-based alloy samples H1a and H1b when used as a wire for forming struts of a stent, and Ni-based alloy samples H2a and H2b when used to form an outer shell substantially surrounding an exemplary tantalum (Ta) inner core for forming a wire for forming struts of a stent. Table III also includes the composition concentration of the commercial alloy Haynes 230. All of the above exemplary alloy compositions were formulated by mixing powders of the elements and melting the mixed powders.

Mechanical Properties

Figure 3:
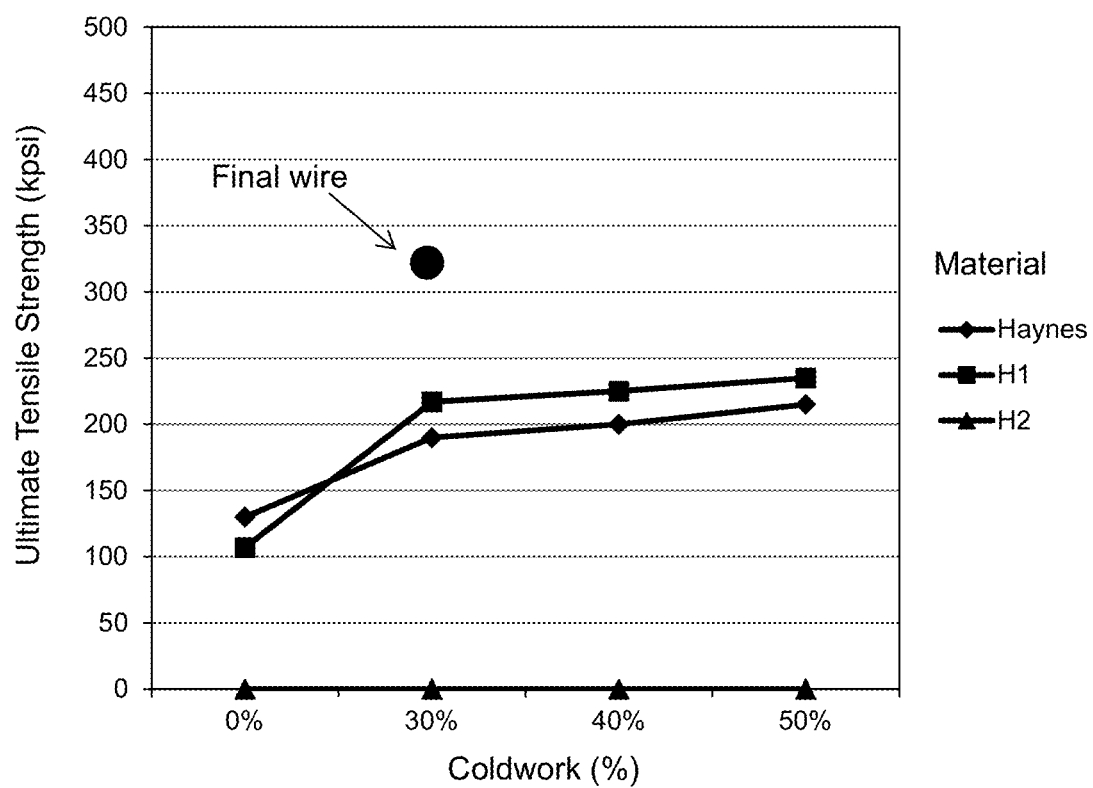
FIG. 3 compares Ni-based alloys/wires in accordance with various embodiments of the invention with a commercially available Ni-based alloy in ultimate tensile strength (UTS) and a function of coldwork.

FIG. 3 compares the mechanical property of ultimate tensile strength (UTS) vs. coldwork % (dislocation strengthening) for a wire using sample H1b in Table III, represented by "H1" in FIG. 3, wherein H1b forms the entire wire and has about 21 weight % Pt. FIG. 3 also compares the UTS vs. coldwork % of a wire formed from Haynes 230, represented by "Haynes" in FIG. 3, which does not contain Pt, but had other similar metal elements as compared with the sample H1b.

As illustrated in FIG. 3, the wire made from the alloy H1b (H1) surprisingly has a similar mechanical property of ultimate tensile strength (UTS) as compared with the conventional Haynes 230 Ni-based alloy (Haynes). As further indicated in FIG. 3, a "final wire" data point indicates the desired coldwork and UTS in the final material.

Table IV lists dimensions, mechanical properties of wires containing sample alloys H1b and H2b having alloy compositions listed in Table III.

TABLE IV

Wires Having Ni-based Alloys

| | H1b Wire | H2b/Ta Composite Wire |
| --- | --- | --- |
| Diameter | 0.084 mm (0.0033 inch) | 0.004 mm (0.0002 inch) |
| Length | 30.000 mm (1.1811 inch) | 30.000 mm (1.1811 inch) |
| Yield strength | 1920 MPa (280 kpsi) | 1200 MPa (175 kpsi) |
| UTS | 2190 MPa (320 kpsi) | 1245 MPa (182 kpsi) |
| Elongation | 3.1% | 0.3% |

Radiopaque Properties

In general, radiography relies on differences in the density of materials being imaged to provide an image contrast between materials. This is because relatively high density materials absorb greater amounts of radiation than low density materials. The relative thickness of each material normal to the path of the radiation also affects the amount of radiation absorbed. For placing stents in smaller vessel lumens, it is desirable to use a stent having a relatively thin cross section or wall thickness, which in turn makes stents of known material less radiopaque and difficult to position in a body lumen. For this reason, the disclosed Co-based alloys are desired at least for providing improved radiopaque properties.

Radiopaque properties of alloys were characterized by calculating mass absorption coefficient of the alloy material. The higher the calculated mass absorption coefficient, the better the radiopacity. For example, theoretical alloy density may be calculated according to the equation:

$$\frac{1}{\rho_{alloy}} = \sum_i \left(\frac{w_i}{\rho_i}\right),$$

while the theoretical mass absorption coefficient may be calculated according to the equation:

$$(\mu/\rho)_{alloy} = \sum_i w_i (\mu/\rho)_i,$$

where $w_i$ is the weight percent of the $i^{th}$ alloying element; $\mu$ is the linear absorption coefficient of the material; $\mu/\rho$ is the mass absorption coefficient; and $(\mu/\rho)_i$ is the mass absorption coefficient for the $i^{th}$ alloying element in the pure state. The mass absorption coefficient, $\mu/\rho$, is constant for a given material and energy of incident radiation.

According to the equations discussed above, Table V lists calculated and actual density as well as calculated mass absorption coefficient of the alloy sample H1b and the conventional alloy Haynes 230 having compositions shown in Table IV at 80 keV and 100 keV, which are in the realm of current C-arm equipment for cardiology.

TABLE V

| Alloys | Calculated Density (g/cm³) | Actual Density (g/cm³) | Calculated Mass Absorption Coefficient (cm²/g) at | |
|---|---|---|---|---|
| | | | 80 keV | 100 keV |
| H1b | 10.34 | — | 3.285 | 1.893 |
| Haynes 230 | 9.10 | 8.97 | 1.685 | 0.984 |

As indicated in Table V, at both 80 keV and 100 keV, the sample alloy H1b containing dense metal member Pt has a calculated mass absorption coefficient higher than the corresponding commercially available Ni-based alloy Haynes 230. The sample alloy H1b provides better radiopacity over Haynes 230.

Example 4

Figure 4:
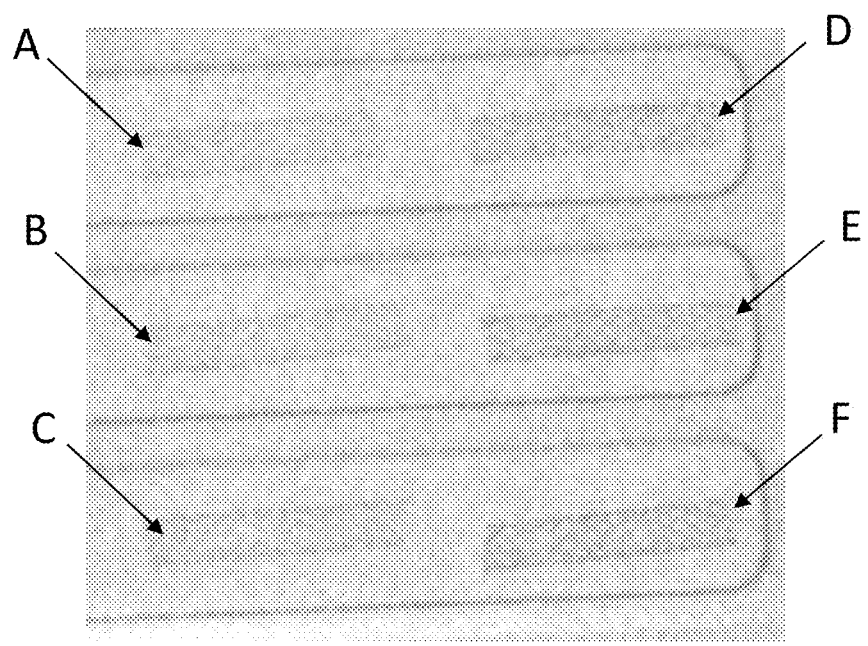
FIG. 4 illustrates differences in radiopacity of stents made from a commercial Co-based alloy and stents made from alloys in accordance with embodiments of the invention.

Identical stents were made from wires having three different thicknesses, including 0.0032 inches (sample A), 0.0034 inches (sample B), and 0.0036 inches (sample C), formed from MP35N LT. In addition, stents were made from wires in accordance with embodiments of the invention, including a wire having a thickness of 0.0036 inches formed from an alloy comprising about 35.2 weight % Co, about 20.1 weight % Pt, about 16.8 weight % Cr, about 17.2 weight % Ni, and about 11.1 weight % Mo (sample D), a wire having a thickness of 0.0034 inches formed from an alloy comprising about 37 weight % Fe, about 30.8 weight % Pt, about 18.4 weight % Cr, about 9.5 weight % Ni, and about 1.5 weight % Mo (sample E), and a wire having a thickness of 0.0033 inches formed from an alloy comprising about 37.1 weight % Ni, about 21 weight % Pt, about 17.7 weight % Cr, about 13.3 weight % W, about 4.9 weight % Co, about 4.4 weight % Fe, and about 2.2 weight % Mo (sample F). The stents were placed in a tray and put under a standard C-arm/fluoroscope used in hospital catheter labs. A layer of lead shielding was placed over the tray to add background noise and illustrate radiopacity differences between the materials, as illustrated in FIG. 4. As illustrated, samples D, E, and F, which all include platinum (Pt), showed a higher level of radiopacity than samples A, B, and C, which were formed from commercially available MP35N LT, which does not include platinum.

Example 5

It is expected that stents fabricated with composite wires having a core-shell structure with an outer shell formed of the commercially available Haynes 230, and an inner core having about 25 wt % Ta to about 45 wt % Ta, or about 25 wt % PtIr to about 41 wt % PtIr, may show similar corrosion properties as stents that are fabricated with solid wires formed from Haynes 230. The composite wires may be melted or alloyed at the end of the stents.

Specifically, it is expected that a stent fabricated from a composite wire having a PtIr core, when melted at the end of the stent, will have no effect on the stent's ability to self-passivate regardless of the percentage used, when compared to a stent formed from Haynes 230. In other words, the Ni-based alloys composed of constituents from Haynes 230 and PtIr should result in a corrosion resistant material that is at least equivalent to commercially available Haynes 230. It is also expected that a stent fabricated from a composite wire having a Ta core, when melted at the end of the stent, will have no effect or may actually improve the stent's ability to self-passivate, when compared to a stent formed from Haynes 230, which may lead to substantially the same or higher corrosion resistance, as compared to a stent formed from Haynes 230.

Example 6

It was desirable to show that the materials in accordance with embodiments of the invention can maintain the appropriate ductility/elongation in the material compared to MP35N, which is an alloy that is commonly used in the manufacture of stents, in view of the amount of strain that the stent material undergoes during its lifecycle (i.e. during crimping, deployment, and loading). In addition, it was desirable to determine the appropriate level of annealing to maximize the ductility in the material, while balancing strength. In this example, wires made from the H1b sample listed in Table III having a diameter of 0.084 mm (0.0033 inches) were tested for mechanical properties after being annealed at different temperatures (850° C., 950° C., 1000° C., and 1050° C.) for different times (6 seconds, 12 seconds, 24 seconds, 30 seconds, 36 seconds, and 42 seconds) and were compared to wires made from MP35N, in accordance with ASTM F562, after being annealed at the same temperatures (850° C., 950° C., 1000° C., and 1050° C.) for different times (6 seconds, 12 seconds, 24 seconds, and 30 seconds).

Figure 5A:
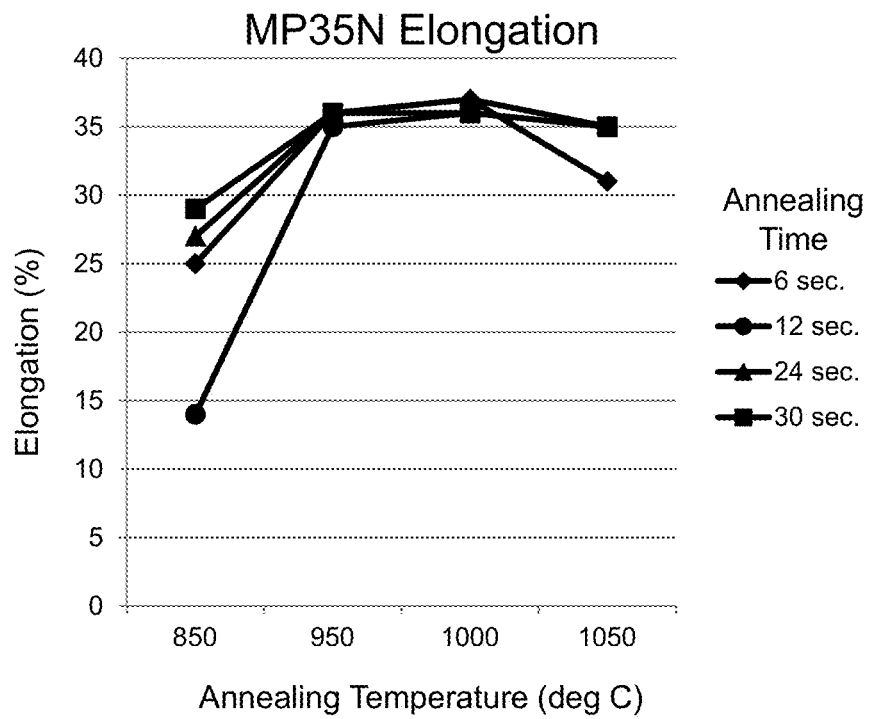
FIGS. 5A and 5B compare the elongation of wires made from a Ni-based alloy in accordance with an embodiment of the invention to wires made from a commercial material used to manufacture stents as a function of annealing temperature and annealing time.
Figure 5B:
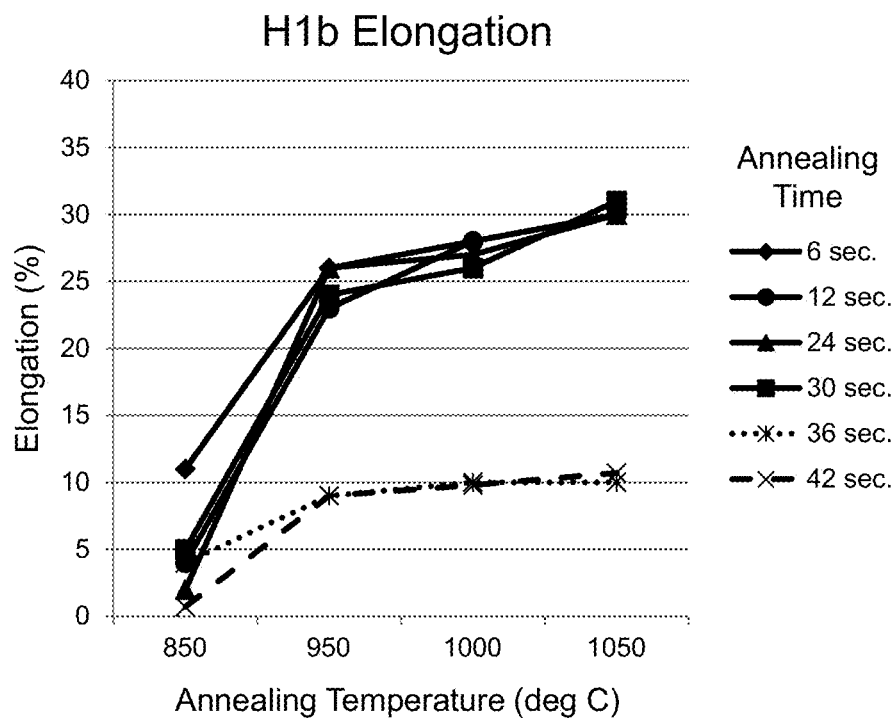
Figure 6A:
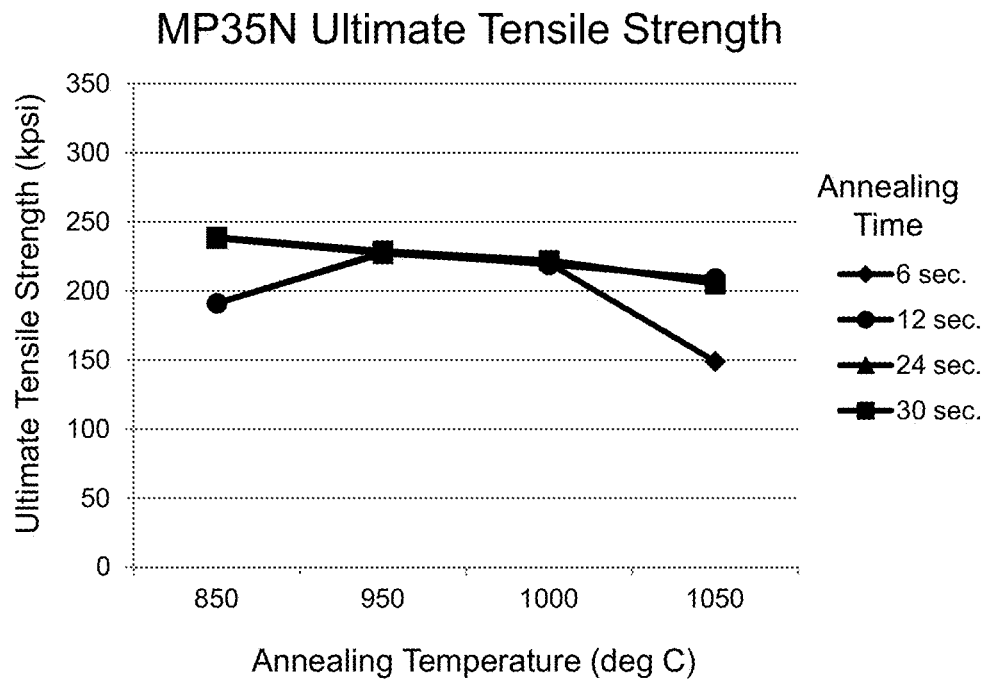
FIGS. 6A and 6B compare the ultimate tensile strengths of the wires made from a Ni-based alloy in accordance with an embodiment of the invention to wires made from a commercial material used to manufacture stents as a function of annealing temperature and annealing time.
Figure 6B:
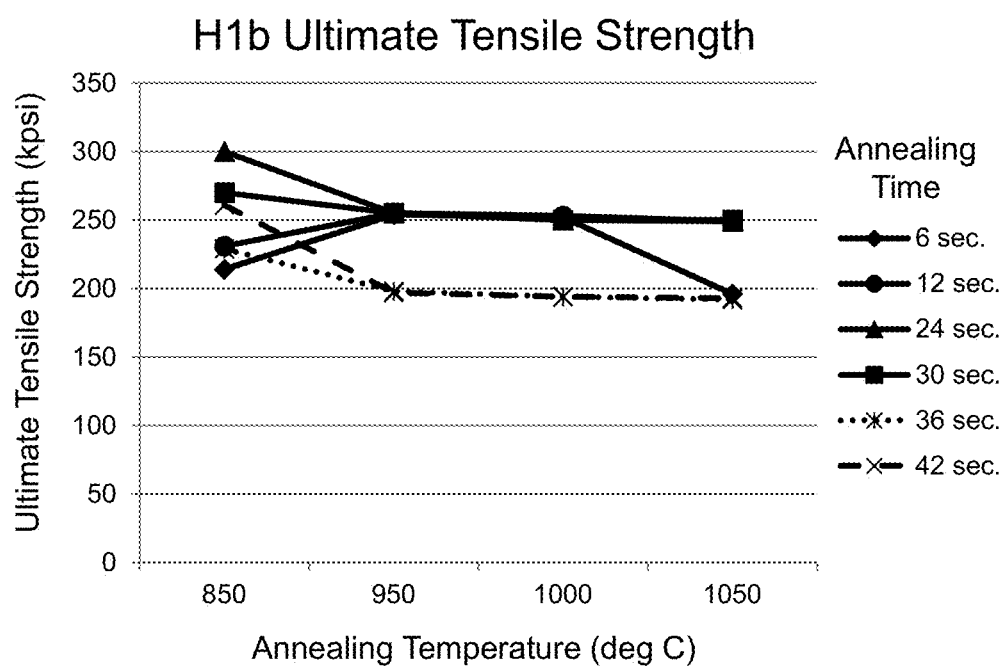
Figure 7A:
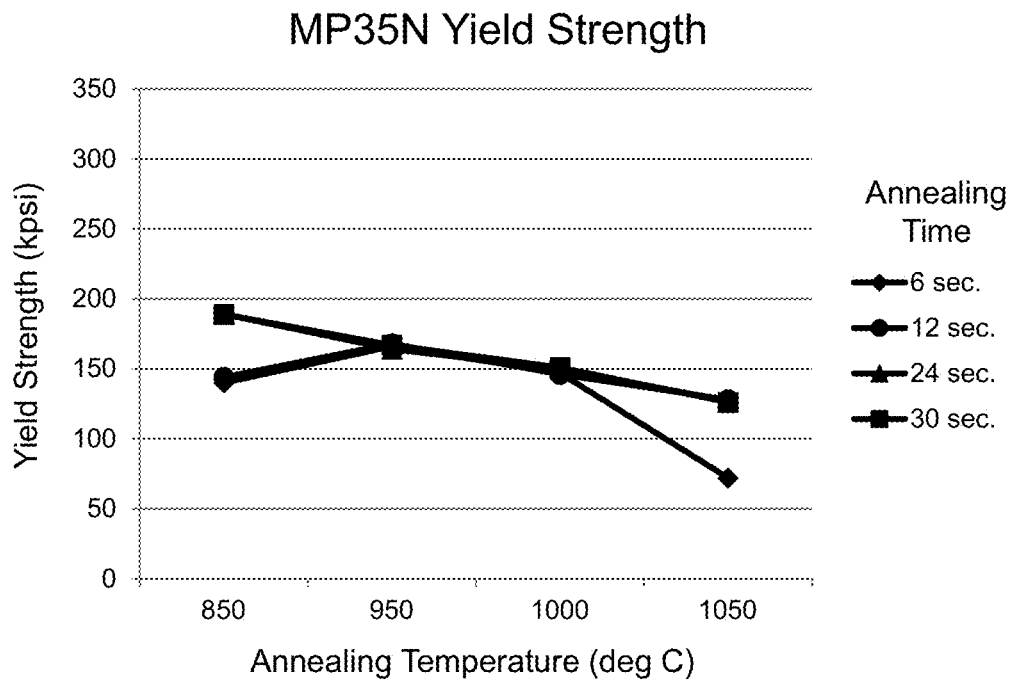
FIGS. 7A and 7B compare the yield strength of the wires made from a Ni-based alloy in accordance with an embodiment of the invention to wires made from a commercial material used to manufacture stents as a function of annealing temperature and annealing time.
Figure 7B:
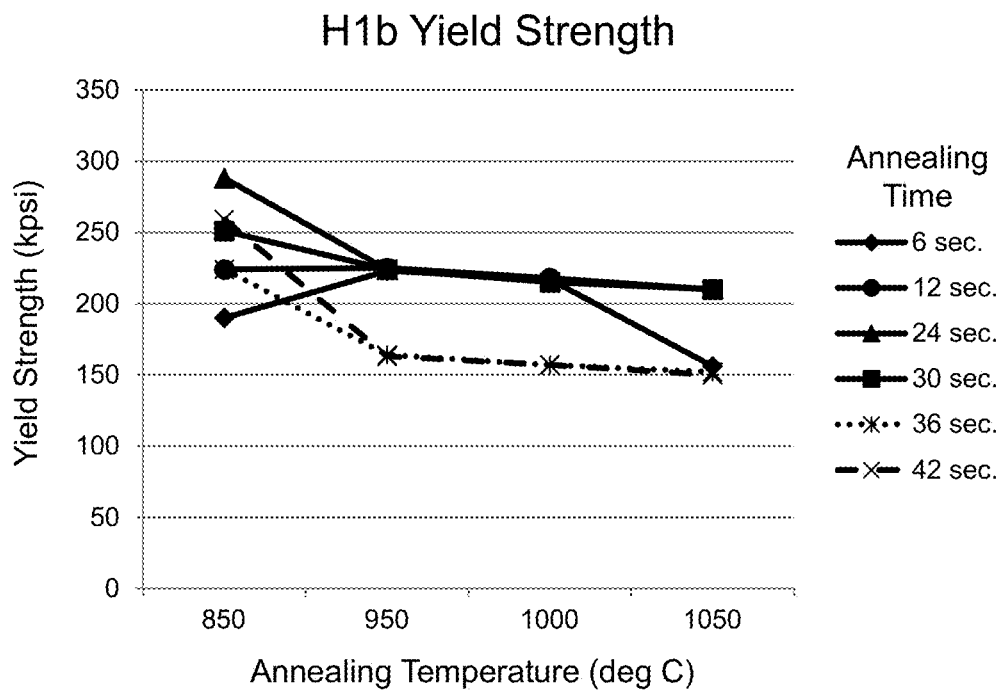

FIG. 5A illustrates the percent elongation that was measured for the wires made from the MP35N alloy as a function of annealing temperature and annealing time, and FIG. 5B illustrates the percent elongation that was measured for the wires made from the H1b alloy sample as a function of annealing temperature and annealing time. FIG. 6A illustrates the ultimate tensile strength (in kpsi) that was measured for the wires of FIG. 5A as a function of annealing temperature and annealing time, and FIG. 6B illustrates the ultimate tensile strength (in kpsi) that was measured for the wires of FIG. 5B as a function of annealing temperature and annealing time. FIGS. 7A and 7B, illustrate the yield strength (in kpsi) that was measured for the wires of FIGS. 5A and 5B, respectively, as a function of annealing temperature and annealing time.

As illustrated, the H1b alloy was able to achieve a ~30% elongation, which indicates the material should have ample ductility for undergoing the strains associated with a stent material during the lifecycle of the stent, after being annealed at 1050° C. In comparison, the MP35N alloy achieved a ~35% elongation. In addition, the ultimate tensile strength of the H1b alloy was generally higher than the ultimate tensile strength of the MP35N alloy for comparable annealing temperatures and times, as illustrated by FIGS. 6A and 6B. Similar results were also found for yield strength, as illustrated in FIGS. 7A and 7B. The testing results indicate that although the ductility of the H1b alloy was lower than the ductility of the MP35N alloy, the H1b alloy is generally a stronger material, as evidenced by the ultimate tensile strength and yield strength that were measured for the wire samples, and appropriate for manufacturing stents.

The wire samples of H1b alloy and MP35N were also tested for Vickers hardness with a test load of 100 g for 10 seconds. The H1b alloy sample with no annealing was measured to have a Vickers hardness of 524. Table VI lists the results of the Vickers hardness test (values in HV) as a function of annealing temperature and time.

TABLE VI

Vickers Hardness Test Results

| | Time | | | | | | | |
|---|---|---|---|---|---|---|---|---|
| | 6 sec. | | 12 sec. | | 24 sec. | | 30 sec. | |
| Temp. | MP35N | H1b | MP35N | H1b | MP35N | H1b | MP35N | H1b |
| 850° C. | 354 | | 425 | 579 | 500 | 562 | 380 | 569 |
| 950° C. | 325 | 402 | 326 | 410 | 321 | 418 | 335 | 408 |
| 1000° C. | 303 | 404 | | 408 | 308 | 404 | 312 | |
| 1050° C. | 279 | 398 | 273 | 398 | 267 | 381 | 279 | 402 |

As shown in Table VI, the H1b alloys were tested to be slightly harder than the MP35N alloy for comparable annealing temperatures and times.

Although stents are described herein, the alloys according to embodiments of the invention may be used for any number of implantable medical devices. While specific embodiments of the invention have been described above, it will be appreciated that the invention may be practiced otherwise than as described. For example, Table I includes additional Examples that were not described in detail, but still fall within the present invention and are claimed below. The descriptions above are intended to be illustrative, not limiting. For example, although the alloys are described as being used to make a stent, it should be appreciated that other medical devices may also be fabricated with such alloys in accordance with embodiments of the invention. Thus, it will be apparent to one skilled in the art that modifications may be made to the invention as described without departing from the scope of the claims set out below.

What is claimed is:
1. A stent comprising:
a nickel-based alloy comprising
10-35 weight % metal member selected from the group consisting of platinum (Pt), gold (Au), iridium (Ir), osmium (Os), rhenium (Re), palladium (Pd), tantalum (Ta), and combinations thereof;
0-6 weight % cobalt (Co);
17-24 weight % chromium (Cr);
13-15 weight % tungsten (W);
0-3 weight % molybdenum (Mo);
0-5 weight % iron (Fe); and
balance nickel (Ni).
2. The stent of claim 1, wherein the nickel-based alloy comprises:
10-25 weight % platinum (Pt);
4-6 weight % cobalt (Co);
17-23 weight % chromium (Cr);
13-15 weight % tungsten (W);
2-3 weight % molybdenum (Mo);
0-3 weight % iron (Fe); and
balance nickel (Ni).
3. The stent of claim 1, wherein the nickel-based alloy is formed of
about 20 weight % platinum (Pt);
about 5 weight % cobalt (Co);
about 22 weight % chromium (Cr);
about 14 weight % tungsten (W);
about 2 weight % molybdenum (Mo);
about 3 weight % iron (Fe); and
balance nickel (Ni).
4. The stent of claim 1, wherein the nickel-based alloy is formed of
about 21 weight % platinum (Pt);
about 5 weight % cobalt (Co);
about 18 weight % chromium (Cr);
about 13 weight % tungsten (W);
about 2 weight % molybdenum (Mo);
about 4 weight % iron (Fe); and
balance nickel.
5. The stent of claim 4, wherein the nickel-based alloy is formed of
about 21 weight % platinum (Pt);
about 4.9 weight % cobalt (Co);
about 17.7 weight % chromium (Cr);
about 13.3 weight % tungsten (W);
about 2.2 weight % molybdenum (Mo);
about 4.4 weight % iron (Fe); and
balance nickel (Ni).
6. The stent of claim 1, wherein the nickel-based alloy forms at least one strut of the stent.
7. The stent of claim 1, wherein the stent comprises a core-shell structure having an outer shell substantially surrounding an inner core, and wherein at least one of the outer shell and the inner core is formed of the nickel-based alloy.
8. The stent of claim 1, wherein the stent comprises a core-shell structure having an outer shell substantially surrounding an inner core, wherein one of the outer shell and the inner core is formed of the nickel-based alloy and the other thereof is formed of a metal member.
9. The stent of claim 8, wherein the metal member comprises a metal selected from the group consisting of platinum (Pt), gold (Au), iridium (Ir), osmium (Os), rhenium (Re), tungsten (W), palladium (Pd), tantalum (Ta), and combinations thereof.
10. The stent of claim 1, wherein the stent comprises a core-shell structure having an outer shell substantially sur- rounding an inner core, and wherein the inner core is hollow and the outer shell is formed of the nickel-based alloy having a thickness of about 0.0010 inches or less.

11. The stent of claim 1, wherein the stent comprises a core-shell structure having an outer shell substantially surrounding an inner core comprising Ta, wherein the outer shell comprises the nickel-based alloy formed of
 about 21 weight % platinum (Pt);
 about 5 weight % cobalt (Co);
 about 18 weight % chromium (Cr);
 about 13 weight % tungsten (W);
 about 2 weight % molybdenum (Mo);
 about 4 weight % iron (Fe); and
 balance nickel.

12. The stent of claim 1, wherein the stent comprises a core-shell structure having an outer shell substantially surrounding an inner core comprising Ta, wherein the outer shell comprises the nickel-based alloy formed of
 about 11.3 weight % platinum (Pt);
 about 5.4 weight % cobalt (Co);
 about 22.9 weight % chromium (Cr);
 about 14.8 weight % tungsten (W);
 about 2.4 weight % molybdenum (Mo);
 about 3.8 weight % iron (Fe); and
 balance nickel (Ni).

13. A stent comprising:
 a plurality of struts formed by a wire, the wire comprising an outer shell surrounding an inner core, wherein at least one of the outer shell and the inner core comprises a nickel-based alloy, the nickel-based alloy comprising
  10-35 weight % metal member selected from the group consisting of platinum (Pt), gold (Au), iridium (Ir), osmium (Os), rhenium (Re), palladium (Pd), tantalum (Ta), and combinations thereof;
  0-6 weight % cobalt (Co);
  17-24 weight % chromium (Cr);
  13-15 weight % tungsten (W);
  0-3 weight % molybdenum (Mo);
  0-5 weight % iron (Fe); and
  balance nickel (Ni).

14. The stent of claim 13, wherein the outer shell comprises the nickel-based alloy, and wherein the inner core is a metal element or a metal alloy, and comprises one or more of platinum (Pt), gold (Au), iridium (Ir), osmium (Os), rhenium (Re), palladium (Pa), tungsten (W), tantalum (Ta), and a combination thereof.

15. The stent of claim 13, wherein the inner core is hollow and the outer shell is formed of the nickel-based alloy having a thickness of 0.0010 inches or less.

16. The stent of claim 13, wherein the outer shell comprises the nickel-based alloy formed of
 about 21 weight % platinum (Pt);
 about 5 weight % cobalt (Co);
 about 18 weight % chromium (Cr);
 about 13 weight % tungsten (W);
 about 2 weight % molybdenum (Mo);
 about 4 weight % iron (Fe); and
 balance nickel.

17. The stent of claim 13, wherein the outer shell comprises the nickel-based alloy formed of
 about 11.3 weight % platinum (Pt);
 about 5.4 weight % cobalt (Co);
 about 22.9 weight % chromium (Cr);
 about 14.8 weight % tungsten (W);
 about 2.4 weight % molybdenum (Mo);
 about 3.8 weight % iron (Fe); and
 balance nickel (Ni).

* * * * *